United States Patent [19]
Jovicevic

[11] Patent Number: 5,129,720
[45] Date of Patent: Jul. 14, 1992

[54] METHOD AND APPARATUS FOR EXAMINATION OF VISUAL ACUITY

[75] Inventor: Bosko Jovicevic, Belgrade, Yugoslavia

[73] Assignee: Angelini Pharmaceuticals, River Edge, N.J.

[21] Appl. No.: 599,672

[22] Filed: Oct. 17, 1990

[30] Foreign Application Priority Data

Oct. 20, 1989 [YU] Yugoslavia .............................. 672/89

[51] Int. Cl.⁵ .............................................. A61B 3/02
[52] U.S. Cl. .................................... 351/243; 351/242; 351/246
[58] Field of Search ................ 351/211, 239, 243, 247, 351/237, 242, 246

[56] References Cited

U.S. PATENT DOCUMENTS 1,852,837  4/1932  Desmond et al. .................... 351/243
2,340,760  2/1944  Leland ................................. 351/243
2,770,999  11/1956  Older ................................... 351/243

Primary Examiner—Rodney B. Bovernick
Attorney, Agent, or Firm—Ladas & Parry

[57] ABSTRACT

A method and apparatus for measuring visual acuity utilizes an apparatus having two rotating charts. The two rotating charts are mounted within a housing which has a window in the front thereof. The housing is illuminated and the charts are placed upon plastic rotating disks which transmit light. The disks are rotated independent of each other in order that one chart may be viewed through the window in the apparatus. Adjacent the window are a series of LEDs which serve to indicate to the patient which line of the optotypes on the chart is to be read. At the bottom of the device there is a display which indicates the number of the line being read and the visual acuity that this represents. The activation of the indicators and the rotation of the disks are controlled via a wireless remote control.

18 Claims, 5 Drawing Sheets

METHOD AND APPARATUS FOR EXAMINATION OF VISUAL ACUITY

BACKGROUND OF THE INVENTION

The present invention relates to a method and apparatus for examination of the visual acuity of a patient.

Examination of visual acuity represents one of the most important tests in ophthalmology. This test is utilized to provide the doctor with information on the existence on eye disease or abnormalities and provides an evaluation of treatment efficiency. Visual abilities include normal vision characteristics which are represented by the conventional 20/20 score of an individual who can read letters at twenty feet designed to be read at that distance. Accurate acuity measurements are required for vision evaluations or for scientific study where the results are reproducible. The required physiological conditions for visual acuity examinations are designated by the Concilium Ophthalmologicum Universale Budapest 1972 and in the recommendations by the National Eye Institute of Bethesda.

Known is an eye chart which is hung on a wall for testing visual acuity. Also known is a projector which projects a series of eye charts onto a screen. These projectors are commonly used by optometrists and opthamologists because they can conveniently display a number of charts. One main disadvantage of these projectors is the need for a darkened room in order to provide good contrast.

SUMMARY OF THE INVENTION

It is a general object of the present invention to produce a method and apparatus for improved visual acuity examinations.

It is another object of the present invention to produce an apparatus which can perform visual acuity examinations in an illuminated room.

A further object of the present invention is to produce a device for visual acuity examinations which is readily transportable.

A still further object of the present invention is to produce a device for visual acuity examinations which can be operated by remote control so that the operator can be located close to the patient while the device is located at the proper distance for the examination.

These and other objects of the invention are provided in accordance with one aspect of the invention by apparatus for examination of visual acuity comprising a housing having a window in a front panel thereof; illumination means mounted in said housing; first and second disks rotatably mounted in said housing between said illumination means and said window, said first and second disks each transmitting light and having optotypes thereon for testing visual acuity; rotation means in said housing coupled to each of said disks for rotating each disk independent of the other.

A further aspect of the invention comprises a method of testing visual acuity of a patient utilizing an apparatus comprising a pair of illuminated disks mounted in a housing, each of said disks having optotypes thereon for testing visual acuity, the method comprising placing a patient in an illuminated room containing an apparatus comprising a pair of illuminated disks having optotypes thereon mounted in a housing; selecting a chart on one of said disks having predetermined optotypes for a visual acuity test; comparing optotypes read by said patient with the optotypes on said chart to determine the visual acuity of the patient.

DETAILED DESCRIPTION

Figure 1:
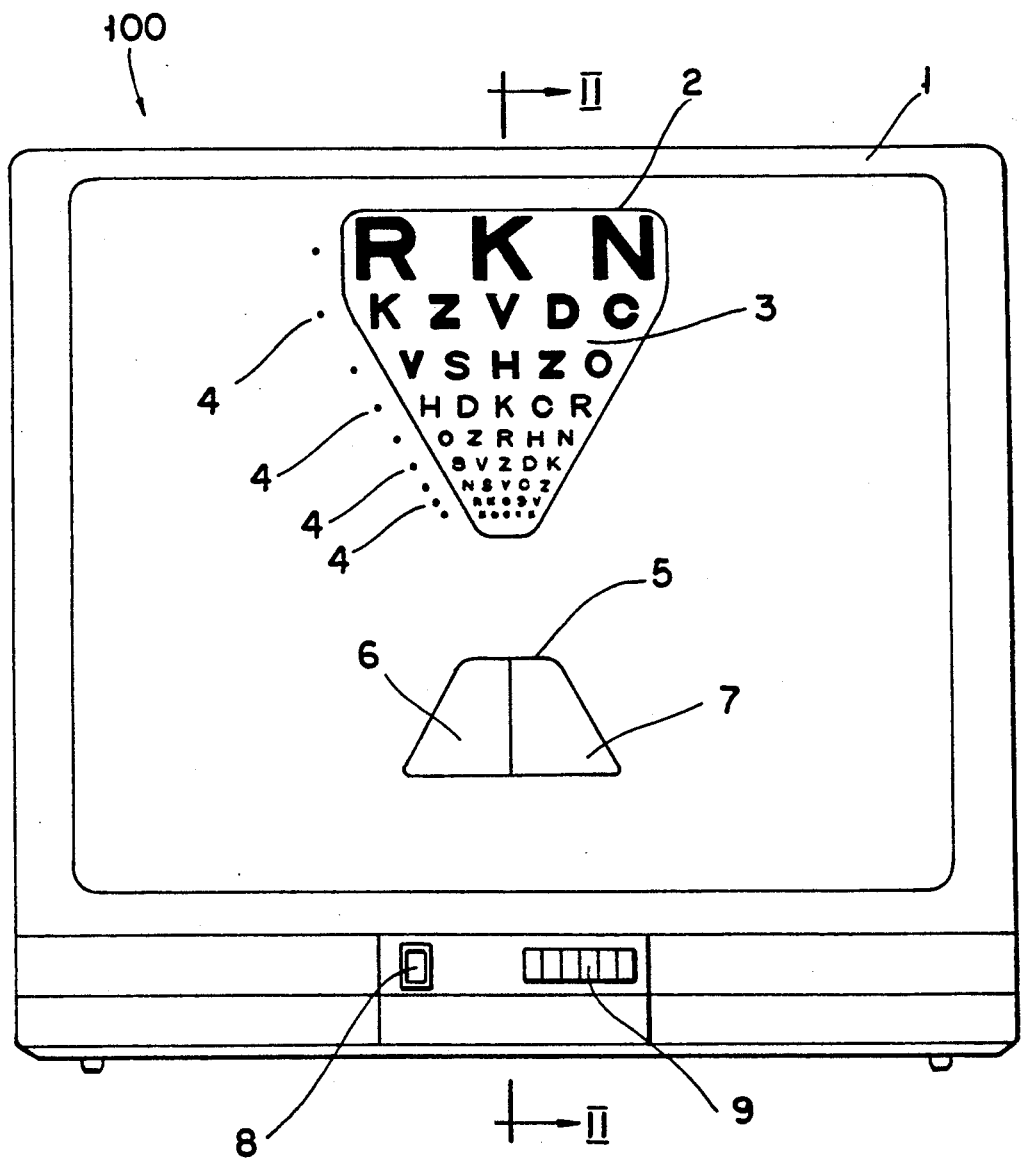
FIG. 1 is a front view of the apparatus in accordance with the present invention.

Referring to FIG. 1, the apparatus is generally shown at 100. The apparatus consists of a box-like housing 1, the front panel of which is shown in FIG. 1. The front panel is provided with two windows for viewing a chart mounted within the housing. The upper window 2 is shaped so as to show only one of the charts 3 within the housing. The window 2 can be an opening in the front of the housing or it can be covered by a clear, colorless covering such as plastic or glass. The lower window 5 is shaped to show a portion of one of the charts 3 mounted within the apparatus. This window is divided into two portions, a left portion 6 and a right portion 7. The left portion 6 is covered with a green filter and the right portion 7 is covered with a red filter so that a bichromatic test can performed. This test is used to test for astigmatism and is important for precise correction of refracting vice. It can be utilized with a chart having Landolt's Rings, for example.

Adjacent to the upper window 2 is a plurality of indicators 4, there being one such indicator for each line of the chart. As shown, the chart comprises nine lines, so that there are nine indicators 4 on one side of the window 2. The indicators may be light emitting diodes (LEDS), for example. The indicators are utilized to indicate to a patient which line of the chart is to be read. Simultaneous with the illumination of an indicator, a number is displayed on the display 9 which indicates the visual acuity that that line represents at a particular distance. These numbers are calculated from Table 1 below. The display 9 can be a LED numeric display, for example.

TABLE 1

| VISUAL ACUITY CALCULATION CHART | | | | | | |
|---|---|---|---|---|---|---|
| Distance | 1 m | 2 m | 3 m | 4 m | 5 m | 6 m |
| Displ. # | | | | | | |
| 1 | 20/600 | 20/300 | 20/200 | 20/150 | 20/120 | 20/100 |
| 2 | 20/300 | 20/150 | 20/100 | 20/75 | 20/60 | 20/50 |
| 3 | 20/200 | 20/100 | 20/65 | 20/50 | 20/40 | 20/33 |
| 4 | 20/150 | 20/75 | 20/50 | 20/40 | 20/30 | 20/25 |
| 5 | 20/120 | 20/60 | 20/40 | 20/30 | 20/25 | 20/20 |
| 6 | 20/100 | 20/50 | 20/53 | 20/25 | 20/20 | 20/17 |
| 7 | 20/85 | 20/42 | 20/28 | 20/21 | 20/17 | 20/14 |
| 8 | 20/75 | 20/37 | 20/25 | 20/19 | 20/15 | 20/12 |
| 10 | 20/60 | 20/30 | 20/20 | 20/15 | 20/12 | 20/10 |

Figure 2:
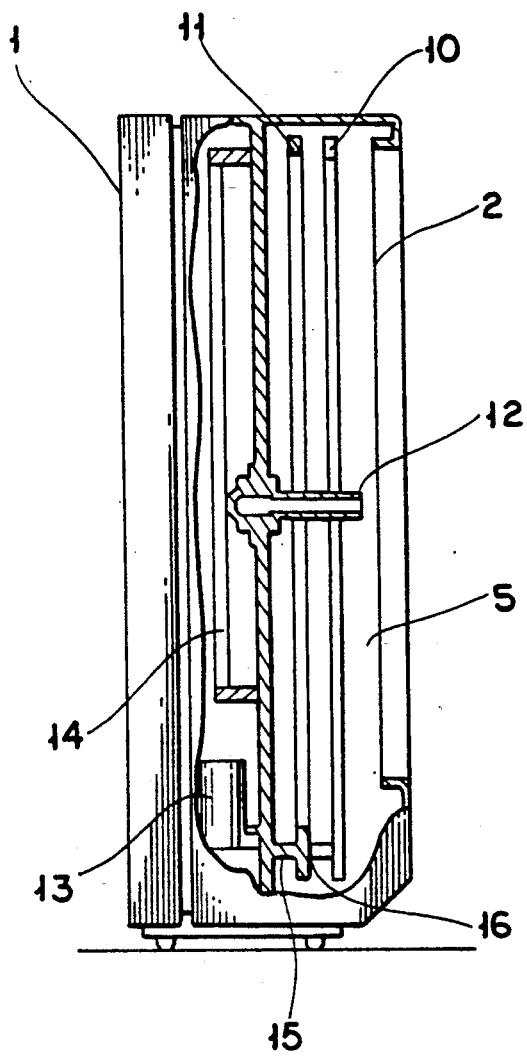
FIG. 2 is a cross-section of the apparatus of FIG. 1 along the lines II—II of FIG. 1 in which part of the housing is shown broken away.

Referring to FIG. 2, the apparatus is shown in cross-section. As can be seen from FIG. 2, the apparatus is composed of two rotating disks which are mounted on for rotation on a horizontal axis 12. The first disk 10 (anterior disk) is located towards the front of the machine as can be seen by its location near the windows 2 and 5 on the front of the machine. The second disk 11 (posterior disk) is located further away from the front of the apparatus. Each of the disks is rotated by a small electric motor. Electric motor 13 turns axle 15 on which a friction wheel 16 is mounted which engages the periphery of disk 11. A similar motor and friction drive is provided for disk 10 but is not shown in FIG. 2. The interior of the box is illuminated by two fluorescent lamps 14 in order to produce a homogeneous and equal lighting within the box. These fluorescent lamps may be standard 20 watt fluorescent lamps which are commercially available and provide a total of 40 watts of illumination within the housing.

Figure 3A:
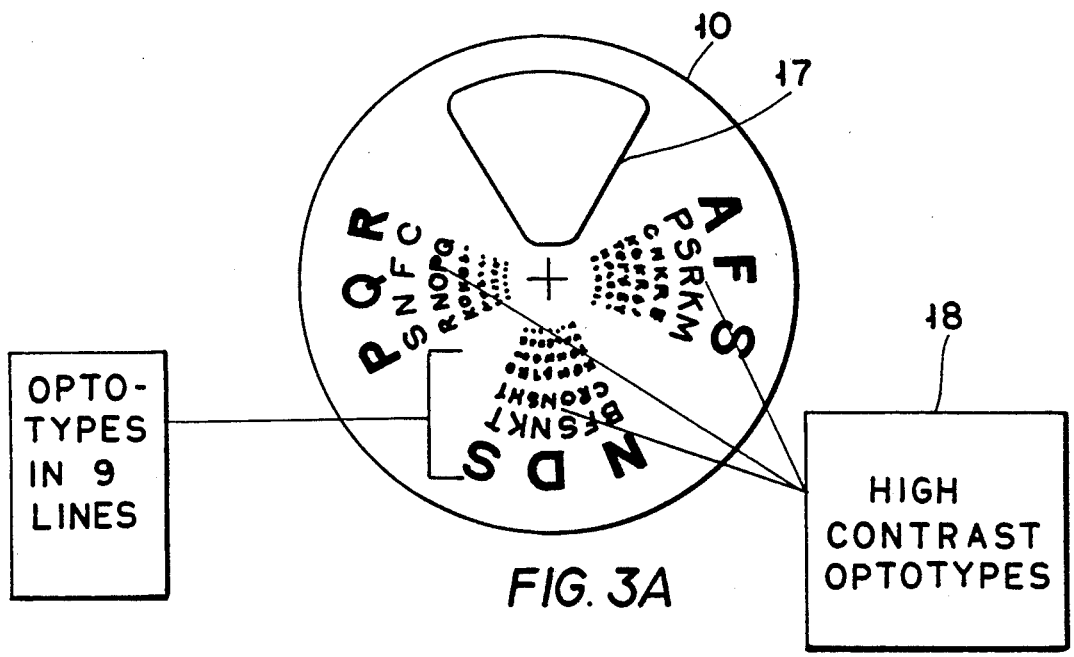
FIG. 3a is a front view of the first (anterior) disk.

Referring now to FIG. 3a, the front or anterior disk is shown. As illustrated, the disk has three optotypes thereon. Each of these optotypes is in one quadrant of the circular disk. A fourth quadrant contains an opening the size of the chart through which the optotypes printed on the rear disk can be viewed. The disk is made of a plastic material such as Plexiglass (trademark) plastic plates. The charts may comprise Sloan Letters, Landolt Rings, Snellens Symbols or numeric optotypes. As illustrated in FIG. 3a, the optotypes are on nine lines wherein the progression of letter height from line to line is geometric. The anterior disk has a high level of contrast with more than 95% contrast sensitivity.

Figure 3B:
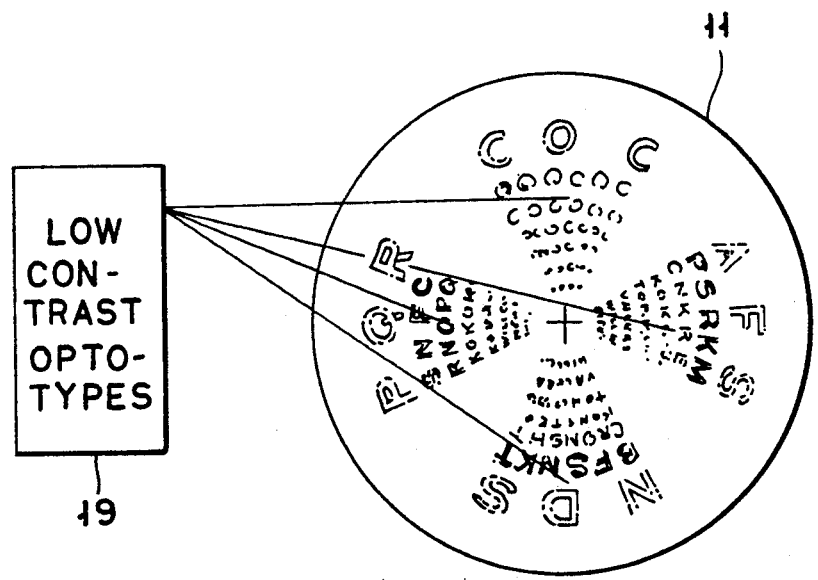
FIG. 3b is a front view of the second (posterior) disk utilized in the apparatus of FIG. 1.

FIG. 3b shows the rear or posterior disk 11 which is very similar to the front or anterior disk 10. A main difference, as seen from FIG. 3b, is that there is no opening in the disk so that 4 charts can be placed on the disk. In addition, low contrast optotypes are utilized which have less than a 10% contrast sensitivity. The utilization of such low contrast sensitivity charts is very important in establishing early diagnosis of cataracts because scattering of light through the lens opacity reduces the contrast of the image. It is also an important screening test for glaucoma when a patient has a depressed contrast sensitivity before a loss of visual field or cupping. In neuroophthalmology, it is important for the diagnosis of multiple sclerosis, intra-cranial tumors and optic nerve lesions. It may also be also used in detecting suppression in cases of amblyopia and may illustrate treatment progress.

The two disks 10 and 11 are mounted about axis 12 for rotation thereon by conventional techniques. The disks are rotated by a pair of electric motors which frictionally engage the periphery of the disk. The electronic circuitry for controlling the electric motors is conventional in design and well known to those skilled in the electronic arts. In addition, the circuitry needed to activate the indicators 4 and the display 9 are conventional and well known to those skilled in the art. Accordingly, this circuitry need not be discussed in detail here.

In operation, each of the disks can be rotated independent of the other to cause one of the appropriate charts to appear in the upper window 2. The fluorescent lamps are illuminated and the optotypes on the charts can be seen by the patient through the window 2. When the posterior disk 11 is to be utilized, the opening 17 on the anterior disk 10 is placed in the window so that the anterior disk does not interfere with the reading of the posterior disk. When the anterior disk is to be read, the low contrast optotypes with less than 10% contrast transmit light easily and do not interfere in any way with the disk in front. An indicator is illuminated to indicate to the patient which line is to be read and, simultaneously, the visual acuity indicated by being able to read this line is displayed in display 9. The display can also display numbers from 1-10 which correspond to the line which is being read on the chart.

A bichromatic test can be utilized by reading the charts which appear in the lower window 5, which may consist of Landolt's Rings.

Figure 4:
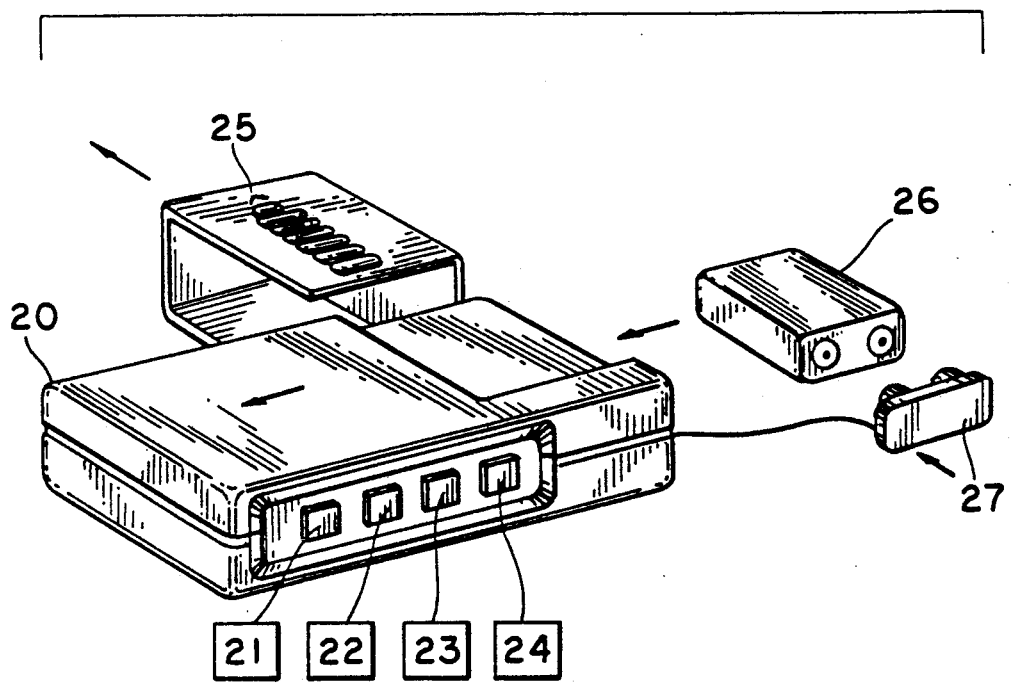
FIG. 4 is a perspective view of a remote control for utilization with the apparatus of FIG. 1.

In order to make the apparatus more convenient for the operator, the operation of the unit is controlled via remote control. Preferably the remote control is a wireless remote control. The wireless remote control may utilize any of the known technologies including radio, ultrasonics, or infra-red to transmit the information from the remote control unit to the apparatus. Such circuitry is well know to those skilled in the art and need not be described in detail here. Referring to FIG. 4, a remote control for utilization with the apparatus is shown. The remote control 20 is powered by a small battery 26, secured under cover 25, and electrically connected to the circuitry via connector 27. It has four buttons 21-24 for operating the apparatus. By activating button 21, the LEDs are activated sequentially from the top of the unit towards the bottom of the unit, that is, from larger to smaller letters. Simultaneously the numbers in the display 9 are changed to match the illuminated indicator. Button 22 activates the indicators 4 in the reverse sequence, that is, from bottom to top as well illuminating the proper numbers in the display 9. Button 23 activates the rotation of the anterior disk 10 and button 24 activates the rotation of the posterior disk 11. The disk may be rotated one quarter of a revolution (90°) each time the button 23, 24 is activated.

Figure 5:
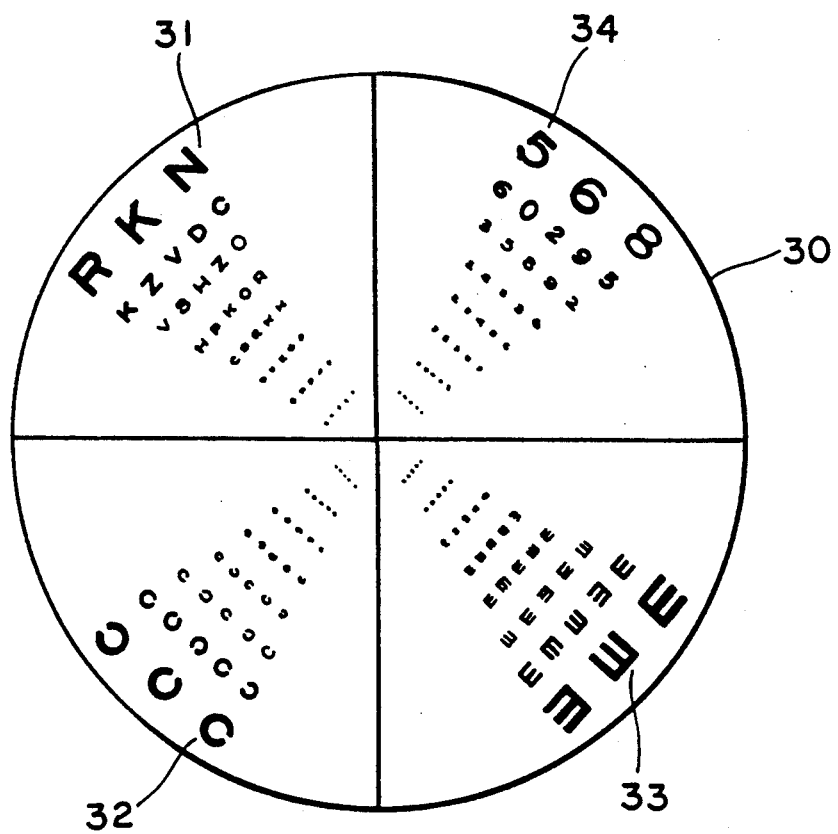
FIG. 5 is an optional optometric chart for use with the apparatus of FIG. 1.

FIG. 5 illustrates an alternative optometric chart for utilization as one of the disks 10 or 11. As shown on disk 30, chart 31 is Sloan's Letters, chart 32 is Landolt's Rings, chart 33 is Snellen's Signs and chart 34 is numeric optotypes.

The apparatus is easily transportable and may be mounted on a mobile cart. It allows for the examination of visual acuity at a distance ranging from one to six meters or approximately three to twenty feet, which makes it ideal for testing patients with either higher or lower visual acuity values than normal.

While a particular embodiment of the present invention has been disclosed herein, it would be obvious to those skilled in the art that certain changes and modifications can be made to it which are included within the scope of the present invention. For example, it is possible to eliminate the opening 17 on the anterior disk 10. It should be noted that the charts utilize only a portion of the quadrant of the circle on which they are located. Thus by indexing the charts so that they are out of phase and by always rotating the disks a quarter of a turn (90°) at a time, it is possible to keep the charts from interfering with each other without the need for the opening 17. This would allow four charts to be placed on the anterior disk 10 as is the case on the posterior disk 11. All such changes and modifications can be made without departing from the invention as defined by the appended claims.

I claim:

1. Apparatus for examination of visual acuity comprising:

a housing having a window in a front panel thereof;
illumination means mounted in said housing;
first and second disks rotatably mounted in said housing between said illumination means and said window, said first and second disks each transmitting light and having optotypes thereon for testing visual acuity wherein said first disk comprises a high contrast disk having at least substantially 95% contrast sensitivity and said second disk is a low contrast disk having no more than substantially 10% contrast sensitivity, said second disk being mounted behind said first disk whereby said second disk is closer to said illumination means;

rotation means in said housing coupled to each of said disks for rotating each disk independent of the other.

2. The apparatus according to claim 1 wherein said optotypes comprise a plurality of lines if symbols in which the progression of letter size from line to line is geometric.

3. The apparatus according to claim 2 wherein said optotypes comprise four charts, a first chart comprising Sloan Letters, a second chart comprising Landolt Rings, a third chart comprising Snellens Symbols and a fourth chart comprising numeric optotypes.

4. The apparatus according to claim 1 wherein the optotypes are divided into four charts, each chart being in one quadrant of the disk.

5. The apparatus according to claim 4 wherein said charts occupy only a portion of said quadrant.

6. Apparatus for examination of visual acuity comprising:
a housing having a window in a front panel thereof;
illumination means mounted in said housing;
first and second disks rotatably mounted in said housing between said illumination means and said window, said first and second disks each transmitting light and having optotype charts thereon for testing visual acuity;
a second window in said housing, said second window comprising a green and a red filter in front of one of said charts for performing a bichromatic test;
rotation means in said housing coupled to each of said disks for rotating each disk independent of the other.

7. Apparatus for examination of visual acuity comprising:
a housing having a window in a front panel thereof;
illumination means mounted in said housing;
first and second disks rotatably mounted in said housing between said illumination means and said window, said first and second disks each transmitting light and having optotypes thereon for testing visual acuity, said optotypes being of the form of individual charts having lines of symbols and further comprising indicator means at a side of said window adjacent each of said lines of symbols for indicating the lien which is to be read by a patient;
rotation means in said housing coupled to each of said disks for rotating each disk independent of the other.

8. The apparatus according to claim 7 wherein said indicator means comprise a plurality of light emitting diodes (LEDs).

9. The apparatus according to claim 7 further comprising a numeric display for indicating the visual acuity of the line of the chart which is adjacent an illuminated indicator.

10. The apparatus according to claim 1 wherein said illumination means comprises a plurality of fluorescent lamps.

11. The apparatus according to claim 1 wherein said rotation means comprises a pair of electric motors coupled to said disks.

12. The apparatus according to claim 1 further comprising a remote control means for rotating said disks from a location remote from said apparatus.

13. The apparatus according to claim 12 wherein said remote control means is wireless.

14. The apparatus according to claim 7 further comprising a remote control means for rotating said disks from a location remote from said apparatus.

15. The apparatus according to claim 14 wherein said remote control means is wireless and controls said indicator means to illuminate an indicator means to illuminate an indicator adjacent a lien of symbols which said patient is to read.

16. Method of testing visual acuity of a patient utilizing an apparatus comprising a pair of illuminated disks mounted in a housing, each of said disks having optotypes thereon for testing visual acuity, the method comprising:
placing a patient in an illuminated room containing an apparatus comprising first and second illuminated disks having optotypes thereon mounted in a housing; said first disk comprising a high contrast disk having at least substantially 95% contrast sensitivity and said second disk comprising a low contrast disk having no more than substantially 10% contrast sensitivity, said second disk being mounted behind said first disk whereby said second disk is closer to illumination means in said apparatus;
selecting a chart on one of said disks having predetermined optotypes for a visual acuity test;
comparing optotypes read by said patient with the optotypes on said chart to determine the visual acuity of the patient.

17. The method according to claim 16 wherein the selecting step comprises:
activating a wireless remote control means for activating an electric motor in said apparatus;
rotating one of said disks so that a chart appears in a window of said apparatus.

18. The method according to claim 16 further comprising the step of illuminating an indicator adjacent a line of said chart for indicating the line of the chart that the patient is to read.

* * * * *